(12) United States Patent
Muntermann

(10) Patent No.: US 6,197,023 B1
(45) Date of Patent: Mar. 6, 2001

(54) APPARATUS AND PROCESS FOR CATHETER ABLATION

(76) Inventor: Axel Muntermann, Gotenweg 51, D-35578 Wetzlar (DE)

( * ) Notice: Subject to any disclaimer, the term of this patent is extended or adjusted under 35 U.S.C. 154(b) by 0 days.

(21) Appl. No.: 09/053,838

(22) Filed: Apr. 1, 1998

(30) Foreign Application Priority Data

Apr. 1, 1997 (DE) .............................................. 197 13 527
May 22, 1997 (DE) .............................................. 197 21 362

(51) Int. Cl.$^7$ .................................................. A61B 18/18
(52) U.S. Cl. .............................. 606/41; 606/42; 606/45; 607/102
(58) Field of Search .......................... 606/41, 45, 48–50; 607/96–102, 113, 122

(56) References Cited

U.S. PATENT DOCUMENTS

| | | | |
|---|---|---|---|
| 4,936,281 | * | 6/1990 | Stasz . |
| 5,174,299 | * | 12/1992 | Nelson . |
| 5,517,989 | * | 5/1996 | Frisbie et al. . |
| 5,540,681 | * | 7/1996 | Strul et al. .............................. 606/34 |
| 5,588,432 | * | 12/1996 | Crowley . |
| 5,688,267 | * | 11/1997 | Panescu et al. ......................... 606/41 |
| 5,755,760 | * | 5/1998 | Maguire et al. ...................... 607/122 |
| 5,797,905 | * | 8/1998 | Fleischman et al. ................... 606/41 |
| 5,837,001 | * | 11/1998 | Mackey ................................ 607/102 |

\* cited by examiner

Primary Examiner—Linda C. M. Dvorak
Assistant Examiner—Roy Gibson (57) ABSTRACT

An apparatus and a process for catheter ablation, with an ablation catheter and, associated with this, a connection to a high frequency generator, to a controlled or to a regulated high frequency ablation equipment, wherein the catheter has at least one electrode for the ablation of tissue by irradiation of ablating power, preferably of high frequency power and preferably at least one temperature sensor associated with this electrode for the determination of the temperature of the electrode; the energy delivery to the tissue to be ablated is controlled or regulated such that a predetermined coagulation temperature is reached within the concerned tissue region, and a device is provided for the sensing of a parameter which is related to the temperature difference between the temperature measured at the electrode and the temperature in the tissue in the neighborhood of the electrode.

12 Claims, 9 Drawing Sheets

Fig. 6 Dependence of depth of lesion (LT) on the maximum electrode temperature (ET) at different HF-power conditions

Fig. 7

|  | ET<br>x ± SD<br>[°C] | GT (30 s)<br>x ± SD<br>[°C] | GT max.<br>[°C] | LT<br>x ± SD<br>[mm] | GL<br>x ± SD<br>[J] |
|---|---|---|---|---|---|
| KHF | 50 | 40,51 ± 0,4 | 42,5 | 0,9 ± 0,1 | 94 ± 12,8 |
|  | 60 | 46,56 ± 3,1 | 51,5 | 3,5 ± 0,6 | 193 ± 13,5 |
|  | 70 | 57,39 ± 4,0 | 66,5 | 4,7 ± 0,7 | 372 ± 53,8 |
| PHF (70 W) | 50 | 39,9 ± 1,0 | 44,0 | 1 ± 0,1 | 214 ± 17,9 * |
|  | 60 | 49,7 ± 1,8 * | 56,5 * | 4,3 ± 0,5 | 405 ± 58,0 * |
|  | 70 | 63,0 ± 1,2 * | 73,5 * | 7,0 ± 1,1 * | 608 ± 115,9 * |
| PHF (110 W) | 50 | 41,5 ± 0,5 | 47,5 * | 1,9 ± 0,5 * | 243 ± 21,8 * |
|  | 60 | 52,1 ± 2,7 * | 58,5 * | 5 ± 1,1 * | 416 ± 33,3 * |
|  | 70 | 77,8 ± 10.9 * | 94,9 * | 8,6 ± 2,0 * | 718 ± 107,6 * |

FIG. 8

APPARATUS AND PROCESS FOR CATHETER ABLATION

BACKGROUND OF THE INVENTION

1. Field of the Invention

The invention relates to an apparatus for catheter ablation in general and for radiofrequency catheter ablation of preferably living endomyocardial tissue in particular, and also to a corresponding ablation catheter and a process for its operation.

2. Discussion of Relevant Art

In the treatment of cardiac arrhythmias which are produced by electrically autonomous tissue and in particular by tissue which is not subject to the central excitation control of the heart, thermal coagulation of the tissue concerned has been shown to be successful, and is well-established in the field. In this procedure, the ablation catheter is pushed endocardially into the heart, and energy is delivered to the concerned tissue from an electrode at the tip of the catheter or from electrodes arranged along the longitudinal axis of the catheter, so that a local coagulation takes place and the tissue region causing the disturbed functioning is electrically isolated. In this procedure, the energy is usually delivered continuously to the electrode by means of a high frequency generator at frequencies of 300–700 kHz, and a coagulation scar is thus produced to a depth of 3–5 mm.

However, it is disadvantageous for this process that the temperature of some portions of the catheter is so high that blood coagulates and adheres to the catheter. Further ablation is thereby hindered, and cleaning of the electrode is necessary. The subsequent withdrawal and reinsertion of the catheter represents an additional stress for both the patient and the surgeon. Furthermore, there is great danger of thrombosis due to the coagulated blood. On the other hand, there is a requirement to further increase the energy delivered to the tissue, in order to reach, with greater depths of lesion, arrhythmogenic tissue regions which lie deep in the myocardium.

SUMMARY OF THE INVENTION

The invention has as its object at least to mitigate such disadvantages in the catheter ablation of tissue, and to control the delivery of energy to the tissue to be ablated so that a predetermined coagulation temperature is reached within the concerned tissue region.

This object is attained in a surprisingly simple manner by a radio frequency catheter ablation apparatus having an ablation catheter, a connection to a high frequency generator, and to controlled or regulated high frequency ablation equipment associated with the catheter. The catheter has at least one electrode for ablation of tissue by irradiation of ablating power, and at least one temperature sensor associated with the electrode for sensing the temperature of the electrode. A sensing device senses a parameter that is related to a temperature difference between the temperature measured at the electrode and the temperature in tissue in the vicinity of the electrode.

The invention includes the highly surprising knowledge that the temperature measured at the catheter does not agree in every case with the internal tissue temperature, even when the catheter is closely adjacent to the tissue or is surrounded by it. In the meaning according to the invention, but without any limitation of generality thereby, the internal tissue temperature is the temperature within a tissue region which is 0–20 mm distant from the respective catheter electrode, preferably about 0–8 mm distant.

It was furthermore established that in pulsed ablation processes at higher power levels, i.e., at power levels above about 70 Watts and catheter temperatures above 60° C., the internal tissue temperature can be distinctly higher than the catheter temperature, even to the extent that vaporization or the formation of steam bubbles within the tissue can occur, which in some circumstances can have lethal consequences.

Furthermore the electrode temperature according to the invention, even with high internal tissue temperatures, can be kept in a region in which blood does not coagulate at the electrode and adhere to it. Here use was made of the knowledge that a much greater delivery of energy to the concerned tissue takes place, at a predetermined maximum electrode temperature, when an ablation catheter is used which is operated in a pulsed mode, in comparison with a continuously operated ablation catheter.

For example, about double the energy can be delivered to a tissue section until the predetermined electrode temperature of 60° C. is reached, when using a pulse operated ablation catheter with a pulse duty factor of one to one, than when using a continuously operated ablation catheter. The higher delivery of energy furthermore enables deeper depths of lesion to be attained, so that arrhythmogenic tissue regions which lie deeper in the myocardium can also be included. The required depth of lesion is reached more rapidly by means of the increased energy delivery; depths are even thereby reached which the continuous process cannot reach, and moreover the time required is reduced.

The catheter can advantageously include several selectively drivable electrodes with associated temperature sensors, whereby a linear ablation can be effected. This results in a shorter treatment time and hence reduced stress for the patient, and the separation of the concerned tissue section from the primary conduction system can potentially be more effectively insured by means of such an interruption of the conduction system than by the conventional process.

The circumstance that the internal tissue temperature often reaches uncontrolled high temperatures during pulse operation was taken into account in that, for each ablation catheter, a set of parameters is recorded in a test setup, with simultaneous measurement of the internal tissue temperature in a test body, and the result serves as a basis for calculating the internal tissue temperature for the subsequent ablation in the human heart. The occurrence of uncontrolled internal tissue temperatures which endanger the patient's life can thereby be substantially prevented.

BRIEF DESCRIPTION OF THE DRAWINGS

The invention will be described in detail hereinbelow, with reference to preferred embodiments and by means of the accompanying drawings.

DETAILED DESCRIPTION OF PREFERRED EMBODIMENTS

Figure 8:
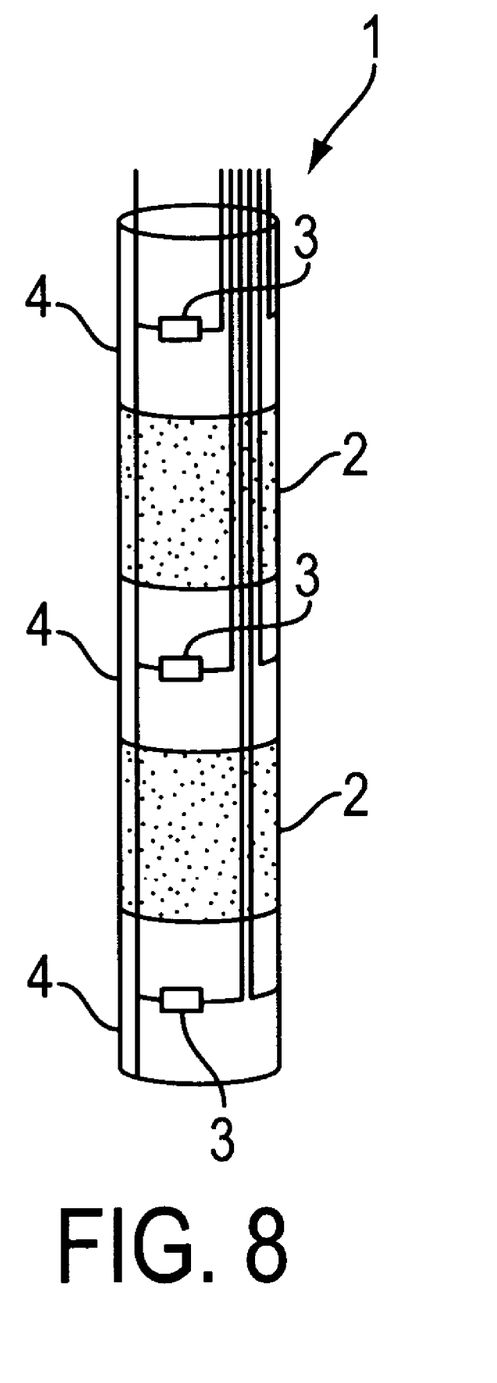
FIG. 8 shows a section of an ablation catheter with several electrodes, suitable for carrying out the invention.

The invention will be described in detail hereinbelow by means of preferred embodiments, and firstly with reference to FIGS. 1 and 8.

The apparatus according to the invention for radio frequency catheter ablation includes in a manner known per se an ablation catheter 1 and, associated with this, a connection to a high frequency generator or a controlled or regulated high frequency ablation equipment. Such an apparatus is described, for example, in International Patent Application PCT/DF/00638, the complete content of which is incorporated herein by reference.

The catheter 1 includes at least one electrode 2 for the ablation of arrhythmogenic tissue, and a temperature sensor 3 associated with this electrode for sensing the temperature of the respective electrode 2. The apparatus furthermore includes a device (not shown in the drawings) for determining the energy which is delivered to the respective electrode 2, and at least one sensor 4 and also a device for sensing the average flow speed of the blood in the surroundings of the catheter 1 or alternatively of the respective electrode 2.

The sensor 4 can consist of an optical fiber which irradiates laser light into the liquid and returns Doppler-shifted back-scattered light signals; the Doppler shift can be sensed interferometrically, and gives information concerning the local or locally averaged flow speed, according to the constriction and arrangement of the outlet openings in the optical fiber.

The sensor 4 can furthermore be a pressure sensor, preferably a piezoelectric back pressure sensor or an ultrasonic sensor; a Doppler shift can likewise be sensed with the latter.

Before the use of the apparatus according to the invention and of the ablation catheter, a set of parameters is determined for the ablation catheter; the catheter 1 is used on a test body 5, and the temperature of the tissue to be ablated is directly measured within the tissue at the respective desired depth, i.e., at a respective desired distance from the catheter, in dependence on various parameters.

The internal tissue temperature is then determined in dependence on the electrode temperature, the pulse power delivered at the respective electrode, and the average flow speed of a solution which has been adjusted to a temperature of about 37° C. and which surrounds the electrode; the internal tissue temperature results are stored as a set of values for the respective individual catheter or for the catheter type. Furthermore, the set of values can be extended, according to the invention, to include the values of the depths of lesion which can be produced.

Figure 1:
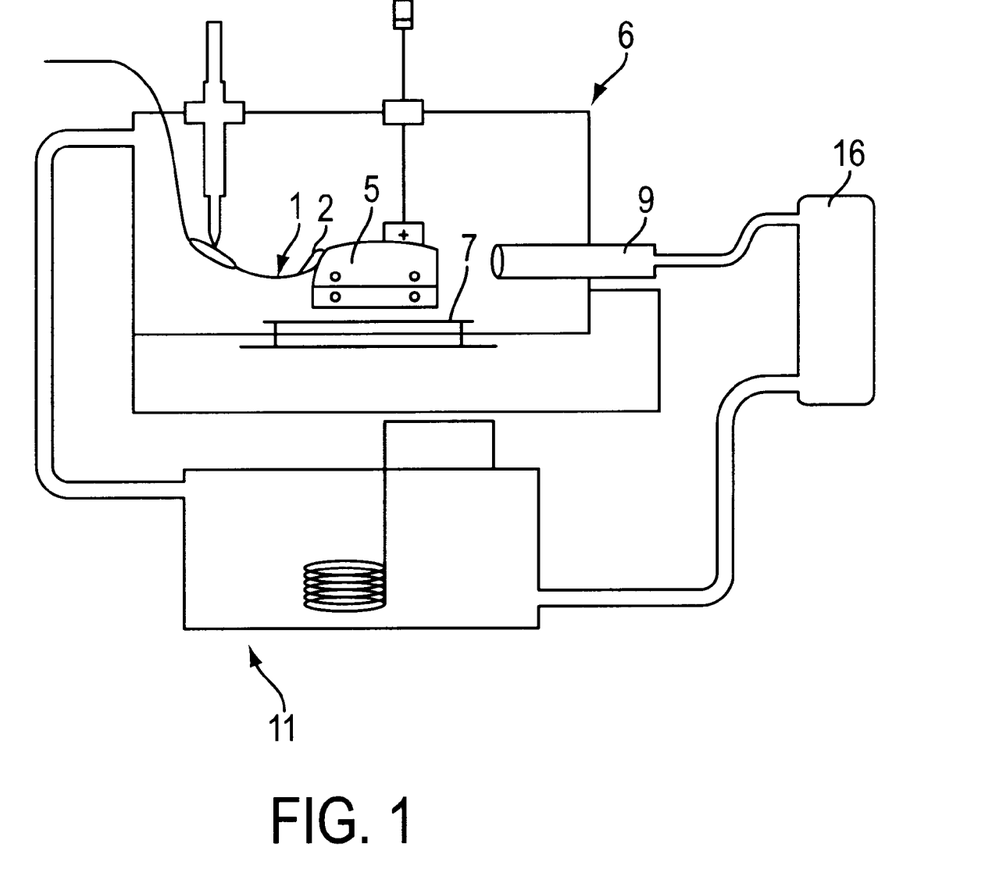
FIG. 1 shows the test setup for the determination of the set of parameters for an individual ablation catheter or a special catheter type.

FIG. 1 shows the corresponding measurement setup. A test body 5 can be installed on the specimen slide 7 in the ablation chamber 6. The ablation catheter 1 is brought up to the test body 5, and an ablation or coagulation of tissue is produced by supplying the respective electrode 2 with a preselected pulse power.

A preferably point-like temperature sensor is introduced directly into the tissue of the test body 5 as far as the desired distance from the catheter, and measures the internal tissue temperature in dependence on the delivered catheter electrode power, i.e., the instantaneous catheter electrode power or the integrated catheter electrode power, in dependence on the respective catheter electrode temperature and in dependence on the flow speed of the blood or of the solution within the ablation chamber 6. For a simulation of the flowing blood in the heart, a nozzle 9 is arranged such that a sodium chloride solution flowing out of the nozzle 9 flows completely around the test body 5 and the catheter 1.

The nozzle 9 is supplied by an adjustable-speed pump (16), which transports the solution out of the chamber 6. The chamber 6 incdicates a regulated immersion heater, which keeps the temperature of the solution preferably to a body temperature of 37° C. The circuit is completed by the return flow of the solution out of the ablation chamber 6 through the lower, heated chamber 11.

Figure 2:
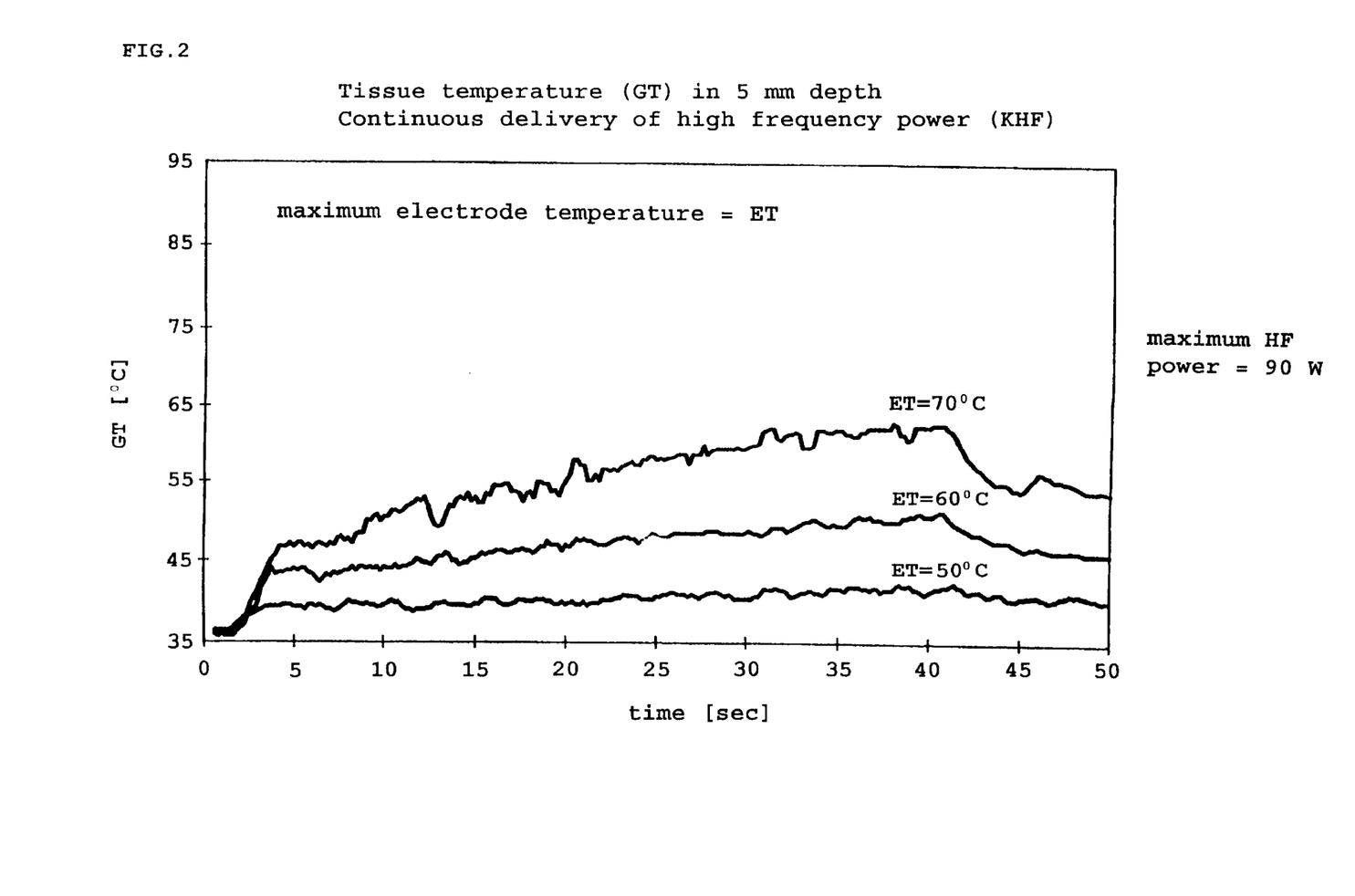
FIG. 2 shows the course of the internal tissue temperature for different maximum electrode temperatures in dependence on time, in a continuous delivery of high frequency power or energy to the electrode at a maximum power of 90 Watt.

FIG. 2 shows the course of the internal tissue temperature GT recorded with this apparatus, in dependence on time, for the case of a continuous delivery of high frequency energy for different maximum electrode temperatures ET. The maximum possible HF power was 90 Watt. As can be seen, the internal tissue temperature rises to about 61° C. within a time of 10 seconds, at a maximum possible electrode temperature of 70° C.

Figure 3:
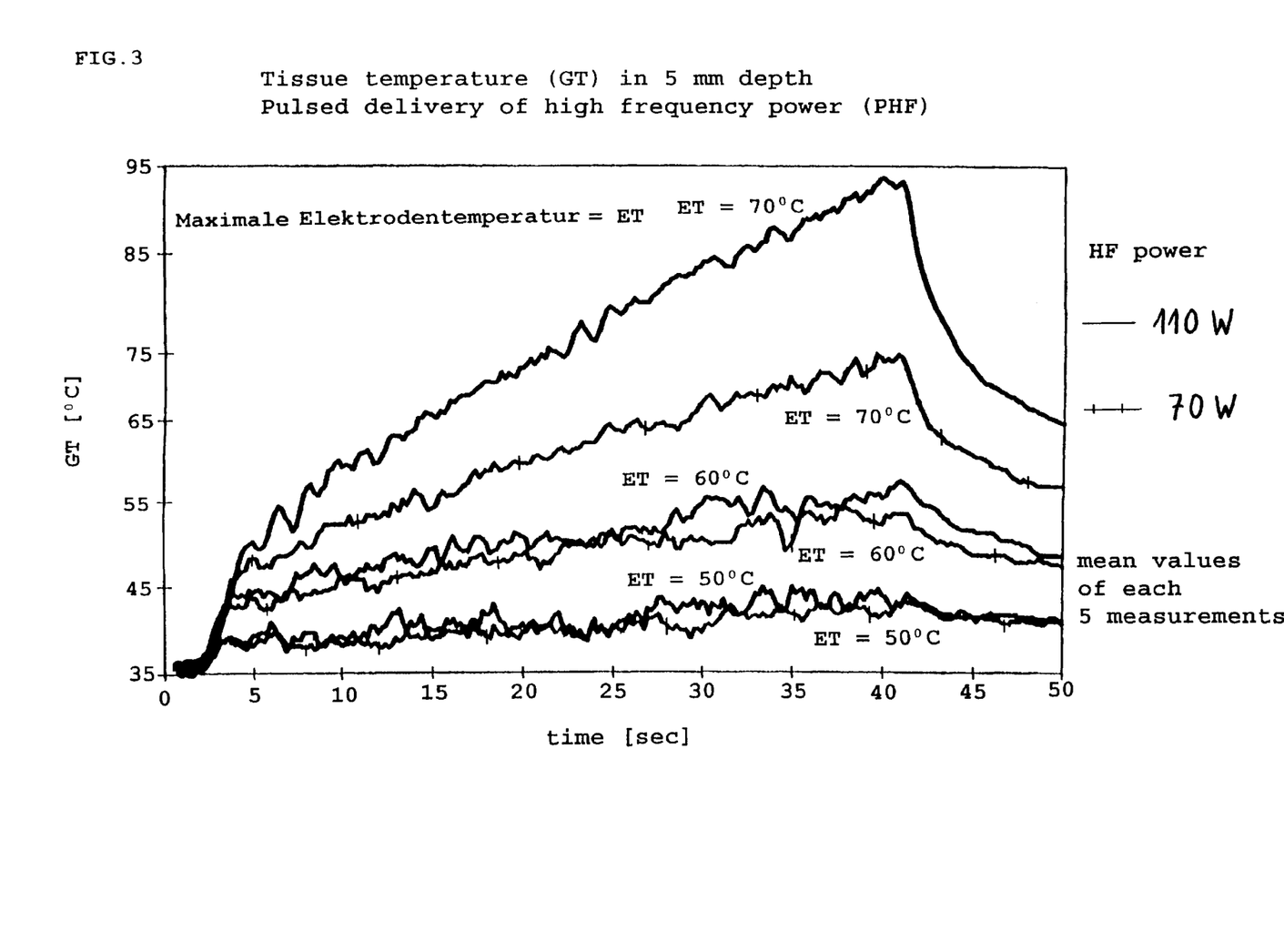
FIG. 3 shows the course of the internal tissue temperature for different maximum electrode temperatures in dependence on time, in a pulsed energy delivery with pulse width modulated pulses at a maximum instantaneous power of 70 and 110 Watt.

In comparison with this, FIG. 3 shows the measured internal tissue temperature GT in dependence on time, with a pulsed HF energy delivery to the electrode 2; the measurement was again carried out and recorded for different maximum electrode temperatures ET. Furthermore, the course of the internal tissue temperature GT is shown for different HF powers.

It can be clearly seen that, with a pulsed delivery of energy at a maximum possible electrode temperature of 70° C., a rise of the internal tissue temperature up to about 72° C. is reached when the HF power is 70 Watt.

With an increase of the HF power to 110 Watt, at the same maximum electrode temperature of 70° C., in a most surprising manner an internal tissue temperature of about 93° C., i.e., close to boiling point, was reached alter 40 seconds. The potential formation of bubbles of steam within the tissue would already have to be taken into account here. The present invention makes it possible for the first time to recognize these dangerous regions, and to exclude them by a consideration of the measured values.

Figure 4:
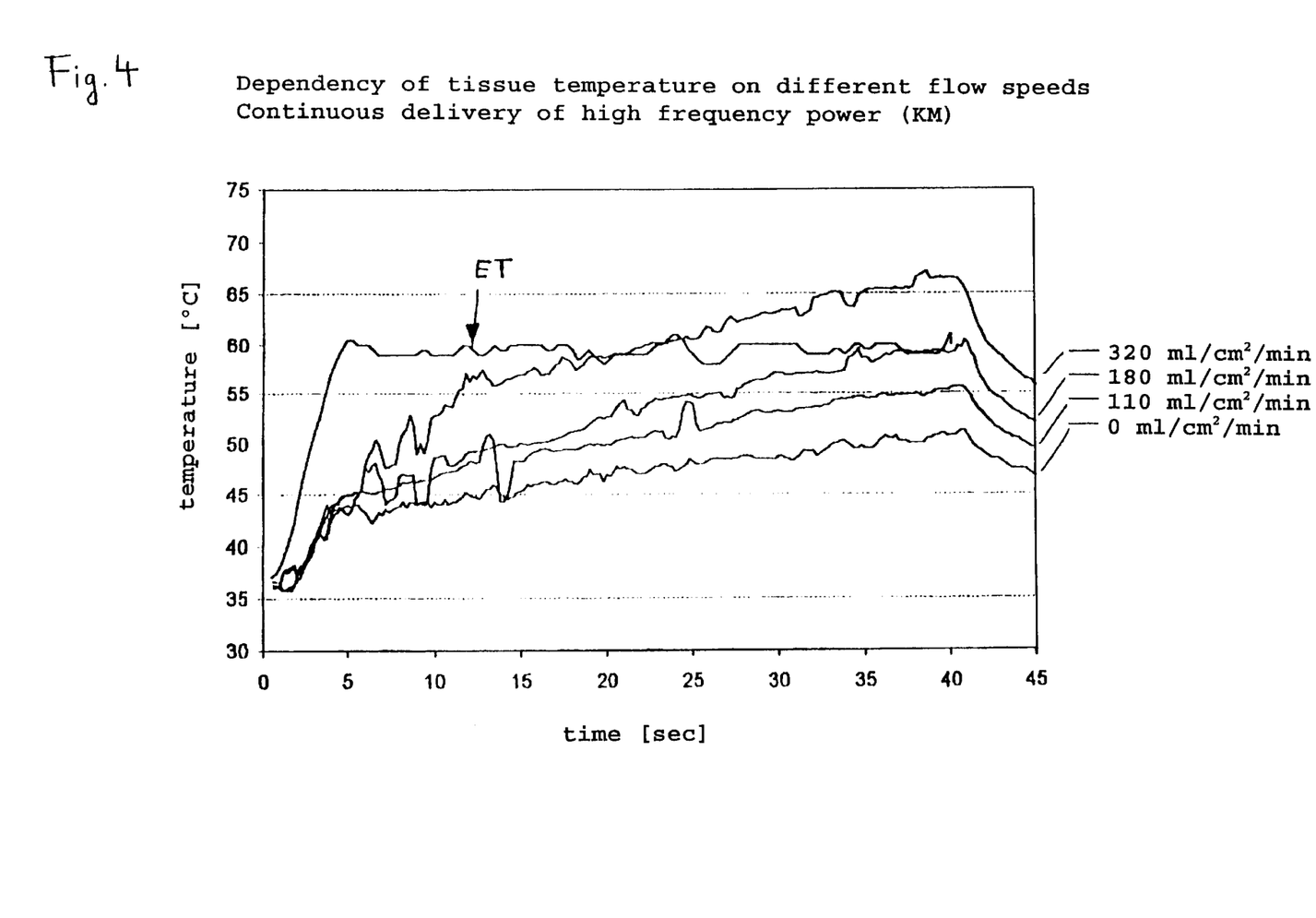
FIG. 4 shows the course of the internal tissue temperature in dependence on time, with a maximum electrode temperature of 60° C., for different flow speeds of a sodium chloride solution surrounding the electrode, with a catheter electrode supplied with continuous high frequency power.
Figure 5:
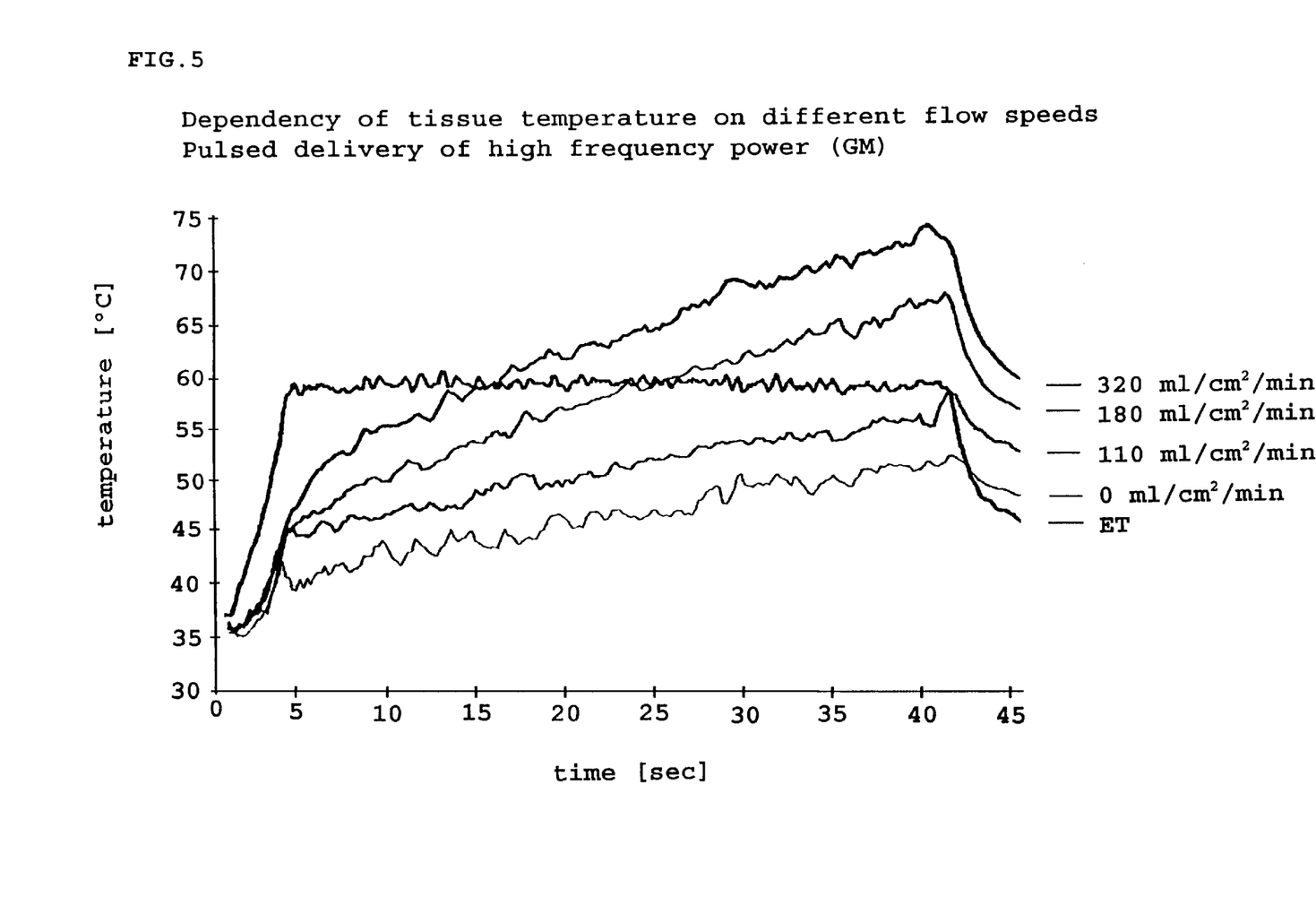
FIG. 5 shows the course of the internal tissue temperature in dependence on time, with a maximum electrode temperature of 60° C., for different flow speeds of a sodium chloride solution surrounding the electrode, with a catheter electrode supplied with pulsed high frequency power.

FIGS. 4 and 5 show the influence of the flow speed of the solution on the energy delivered to the tissue of the test body 5. The internal tissue temperature is shown there in dependence on time, for different flow speeds of the solution. Here also it can be recognized that distinctly higher internal tissue temperatures are reached with pulsed energy delivery (FIG. 5) in contrast to continuous energy delivery (FIG. 4), at the same respective catheter electrode temperature of 60° C.

The higher the speed, and thus the cooling of the electrode, the higher is the delivered power, and therewith the maximum attainable internal tissue temperature; for example, at a flow speed, or a flow of 320 ml per $cm_2$ per minute, the internal tissue temperature is about 75° C. after 40 seconds, according to FIG. 5.

Figure 6:
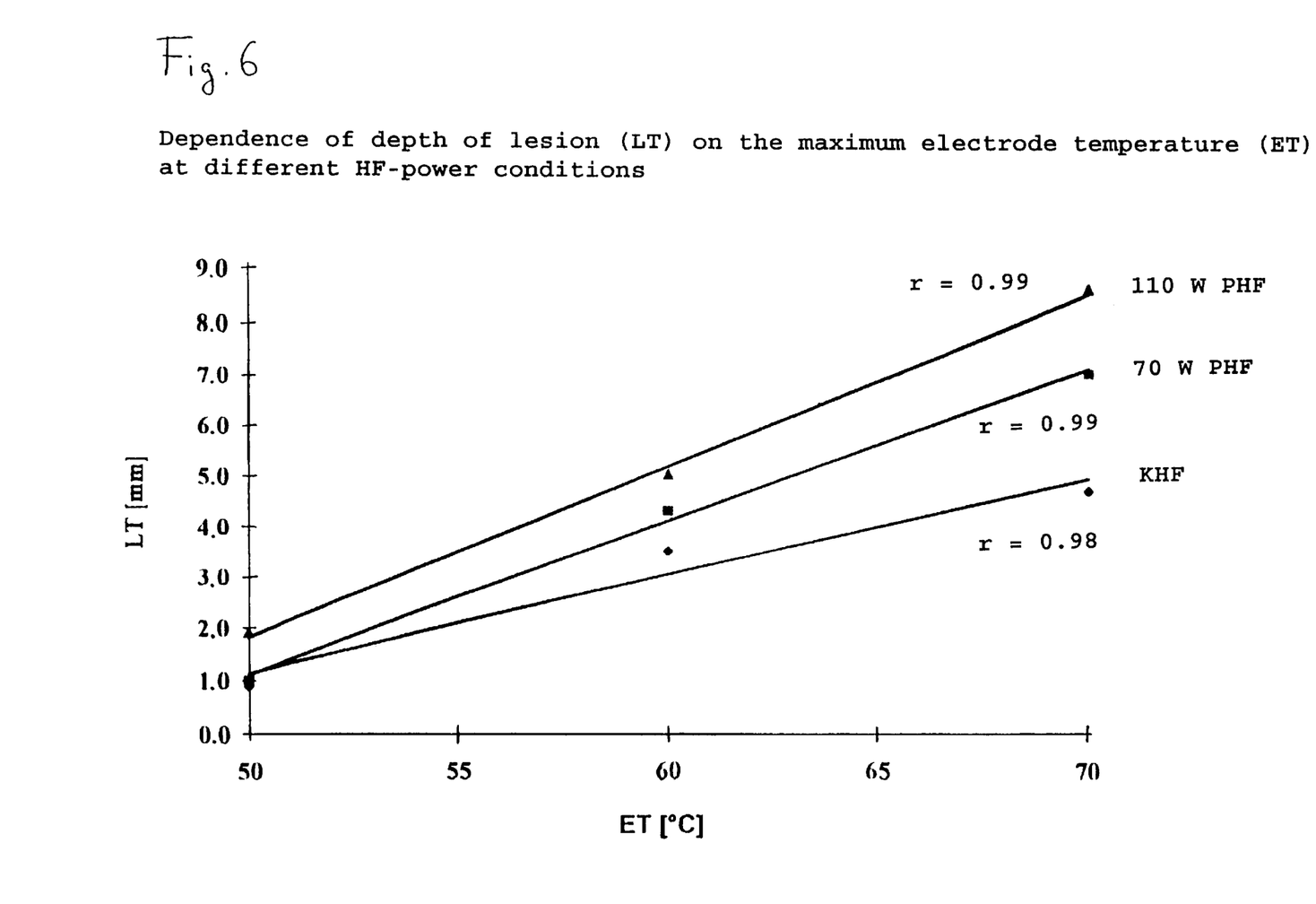
FIG. 6 shows the dependence of depth of lesion on the maximum electrode temperature at different pulsed current powers.

The depths of lesions are shown in FIG. 6 in dependence on the maximum permitted electrode temperature and the kind of application of HF power. The curve with the smallest rise describes the behavior at a supply of a continuous HF current power (KHF) of 70 Watt. In contrast to this, the curve with the middle rise shows the course when a pulsed HF current power (PHF) of 70 Watt was used. The pulsed mode of operation thus makes possible a substantially greater depth of lesion in comparison with continuous application.

With the pulsed mode of operation, the supply is possible of a HF current power of 110 Watt at a catheter temperature of about 60° C., making great depths of lesion possible. According to the invention, in catheter ablation in the heart of a living patient, a temperature is produced in the tissue which is preferably between 40° C. and 90° C., more preferably between 50° C. and 65° C., and most preferably at 65° C. The catheter temperature then does not exceed a threshold lying between 40° C. and 70° C., in the most preferred embodiment of the invention.

Figure 7:
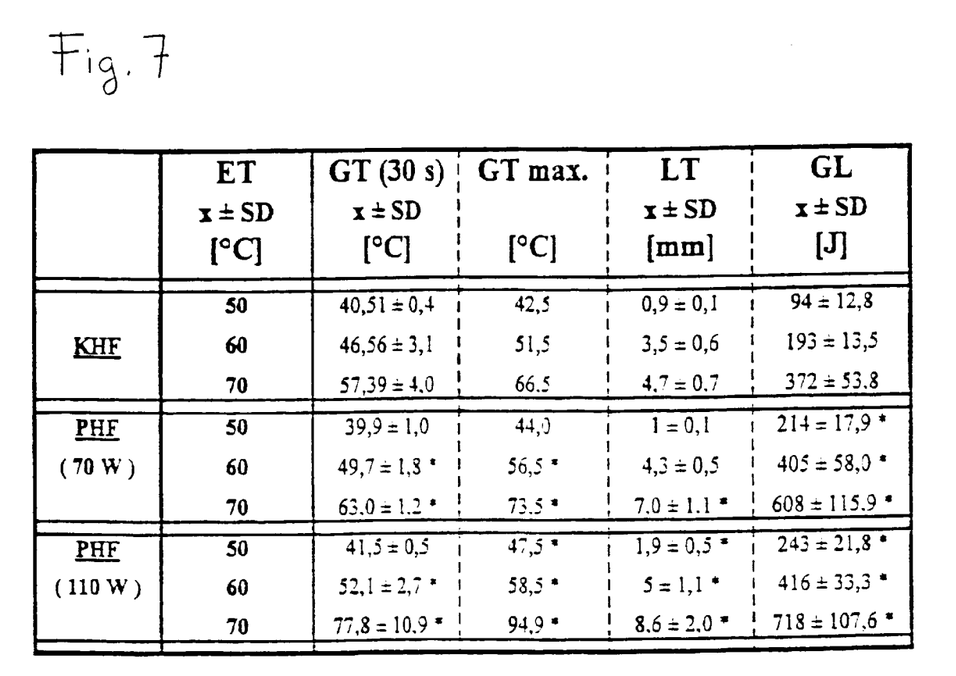
FIG. 7 shows a tabular summary of the lesion values which can be reached according to the invention, in dependence on the catheter temperature and on the delivered ablation power, in a comparison between a continuously operated and a pulsed operated apparatus.

Measurements showed that at a power of 70 Watt about double as much energy is delivered in pulse operation to the tissue to be ablated, in comparison with continuous operation. In this regard, reference is made to the measurement values of FIG. 7, which shows the internal tissue temperature, respectively averaged over the last 30 s of the ablation (GT(30s)), the maximum internal tissue temperature (GTmax), the depth of lesion attained (LT), and the total power delivered (GL; corresponding to the integrated instantaneous power), for continuous operation (KHF) and for pulsed operation (PHF).

The set of values measured with the described apparatus is subsequently used during ablation to determine the internal tissue temperature. For this purpose, the delivered power and the catheter electrode temperature are sensed in an associated measuring and control device (not shown in the drawings) during the ablation process, and the internal tissue temperature is calculated from them.

In a further embodiment according to the invention, the flow speeds, either instantaneous or averaged over time, are sensed by means of the flow speed sensors 4 and are additionally used for a more accurate calculation of the internal tissue temperature.

In general, the catheter temperature can be limited by means of the invention to a maximum value which is preferably free from coagulation, and the time can be sensed after which a maximum internal tissue temperature was reached. The maximum internal tissue temperature can be selected to be far from dangerous values, and can be associated with a desired depth of lesion.

Figure 9:
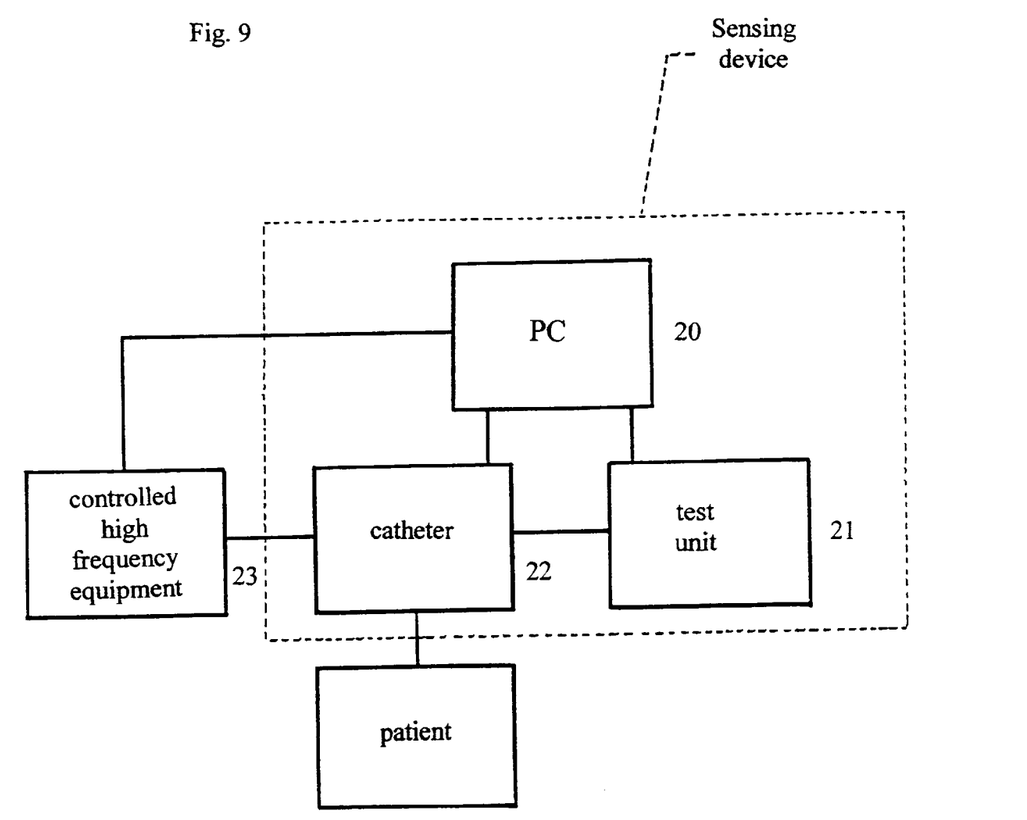
FIG. 9 shows a block diagram of a sensing device according to the invention.

Referring to FIG. 9, it lies within the scope of the invention to handle the measured parameters and also the instantaneously calculated parameters with an external computer unit, in particular with a personal computer (PC20), which communicates with the HF control device. The PC 20 is shown connected to a test unit 21 by which parameters are determined and stored in the PC 20. The parameters are provided to the controlled high frequency ablation equipment 23 for subsequent ablation treatment with a catheter 22. The operator at the PC can then input the desired local associated depth of lesion, and either establish that the delivery of the HF power to the respective electrode is automatically ended or reduced, or that the attainment of the depth of lesion is visually indicated on a monitor, or indicated acoustically, to the operating surgeon, where in the case of such an indication a further ablation devolves on the operating surgeon, who can proceed with this while taking account of the EKG data.

It has furthermore been found that a substantially more uniform lesion can be produced with pulsed energy delivery. Likewise, vaporization, that is, the formation of bubbles of steam, occurs substantially less often than width continuous energy delivery. This is to be attributed to a substantially more uniform temperature distribution in the tissue. In particular, with pulsed energy delivery, the tissue portions as far as about 1 mm to 2 mm depth do not have to be heated so strongly in order to produce deep lesions with a depth of greater than 6 mm.

I claim:

1. Apparatus for catheter ablation, comprising:
an ablation catheter,
associated with said catheter, a connection to a high frequency generator and to controlled or regulated high frequency ablation equipment,
said catheter having at least one electrode for ablation of tissue by irradiation of ablating power, and at least one temperature sensor associated with said at least one electrode for sensing temperature of said at least one electrode, and
a sensing device that senses a predetermined parameter that is related to and takes into account a temperature difference between temperature measured at said electrode and temperature in tissue in the vicinity of said electrode, wherein:
said at least one electrode is driven by energy pulses, depending on previous electrode temperature, delivered energy, and said predetermined parameter sensed by said sensing device, said energy pulses being of fixed or variable length, such that a temperature that can be set in advance is substantially reached in tissue to be ablated, and said at least one electrode temperature does not exceed a predetermined temperature.

2. Apparatus according to claim 1, in which said sensed parameter is power delivered to said tissue in the vicinity of said at least one electrode and said sensing device comprises a power sensing device, and ablation is carried out substantially at a predetermined and regulated catheter temperature.

3. Apparatus according to claim 1, in which said catheter includes several electrodes and several temperature sensors, each of said sensors being associated with a respective electrode and sensing substantially said temperature of said respective electrode.

4. Apparatus according to claim 1, in which said sensing device determines said internal tissue temperature as a function of said temperature measured at said electrode and delivered power and a previously determined set of values that provides temperature relationships in said tissue relative to said temperature measured at said electrode for defined delivered powers.

5. Apparatus according to claim 1, in which said electrode is driven depending on a desired depth of lesion.

6. Apparatus according to claim 1, in which said electrodes are arranged at an end of said catheter.

7. Apparatus according to claim 6, in which a plurality of said electrodes are arranged along an uninterrupted line width a length of up to 7 cm, respectively separated from each other by insulation regions.

8. Apparatus according to claim 1, in which a plurality of said electrodes are driven in a form of pulse width modulation.

9. Apparatus for catheter ablation, comprising:

an ablation catheter, associated with said catheter, a connection to a high frequency generator and to controlled or regulated high frequency ablation equipment, said catheter having at least one electrode for ablation of tissue by irradiation of ablating power, and at least one temperature sensor associated with said at least one electrode for sensing temperature of said at least one electrode, and a sensing device that senses a predetermined parameter that is related to and takes into account a temperature difference between temperature measured at said electrode and temperature in tissue in the vicinity of said electrode, wherein, said catheter has at least one device for sensing instantaneous local or locally average flow speed of blood near said at least one electrode.

10. Apparatus according to claim 9 wherein said at least one device for sensing flow speed of blood is arranged to drive said at least one electrode depending on said flow speed of blood near at least one electrode so that a predetermined temperature is reached in the tissue to be ablated as a function of said catheter, delivered power and flow speed.

11. Apparatus according to claim 9, wherein said at least one electrode is driven, depending on previous electrode temperature and delivered energy, by energy pulses with fixed or variable length, such that a temperature that can be set in advance is substantially reached in tissue to be ablated, and said at least one electrode temperature does not exceed a predetermined temperature.

12. Apparatus for catheter ablation, comprising:

an ablation catheter, associated with said catheter, a connection to a high frequency generator and to controlled or regulated high frequency ablation equipment, said catheter having at least one electrode for ablation of tissue by irradiation of ablating power, and at least one temperature sensor associated with said at least one electrode for sensing temperature of said at least one electrode, and a sensing device that senses a predetermined parameter that is related to and takes into account a temperature difference between temperature measured at said electrode and temperature in tissue in the vicinity of said electrode, wherein said at least one electrode is driven, depending on previous electrode temperature and delivered energy, by energy pulses with fixed or variable length, such that a temperature that can be set in advance is substantially reached in tissue to be ablated, and said at least one electrode temperature does not exceed a predetermined temperature, and wherein, a plurality of said electrodes are driven in a form of pulse width modulation.

* * * * *